(12) United States Patent
Kirschman

(10) Patent No.: US 8,992,587 B2
(45) Date of Patent: Mar. 31, 2015

(54) SPINAL FACET COMPRESSION SCREW WITH VARIABLE PITCH THREAD ZONES AND BUTTRESS HEAD

(75) Inventor: David Louis Kirschman, Dayton, OH (US)

(73) Assignee: X-spine Systems, Inc., Miamisburg, OH (US)

( * ) Notice: Subject to any disclaimer, the term of this patent is extended or adjusted under 35 U.S.C. 154(b) by 0 days.

(21) Appl. No.: 13/184,862

(22) Filed: Jul. 18, 2011

(65) Prior Publication Data

US 2012/0022603 A1    Jan. 26, 2012

Related U.S. Application Data

(60) Provisional application No. 61/365,906, filed on Jul. 20, 2010.

(51) Int. Cl.
*A61B 17/58*   (2006.01)
*A61B 17/86*   (2006.01)
*A61B 17/70*   (2006.01)
*A61B 17/88*   (2006.01)

(52) U.S. Cl.
CPC ........... *A61B 17/863* (2013.01); *A61B 17/7064* (2013.01); *A61B 17/861* (2013.01); *A61B 17/864* (2013.01); *A61B 17/8891* (2013.01)
USPC .......... 606/305; 606/314; 606/315; 606/316; 606/317

(58) Field of Classification Search
USPC .................. 606/300–321; 411/402, 413, 418
See application file for complete search history.

(56) References Cited

U.S. PATENT DOCUMENTS

| | | | |
|---|---|---|---|
| 2,121,193 A | 6/1938 | Hanicke | |
| 2,382,019 A | 8/1945 | Miller | |
| 2,472,103 A | 6/1949 | Giesen | |
| 2,489,870 A | 11/1949 | Dzus | |
| 2,570,465 A | 10/1951 | Lundholm | |
| 2,801,631 A | 8/1957 | Charnley | |
| 3,682,507 A * | 8/1972 | Waud | 411/413 |
| 4,059,102 A | 11/1977 | Devas | |
| 4,175,555 A | 11/1979 | Herbert | |
| 4,456,005 A | 6/1984 | Lichty | |
| 4,463,753 A | 8/1984 | Gustilo | |
| 4,537,185 A | 8/1985 | Stednitz | |
| 4,640,271 A | 2/1987 | Lower | |
| 4,712,957 A * | 12/1987 | Edwards et al. | 411/82.1 |
| 4,858,601 A | 8/1989 | Glisson | |
| 4,944,759 A | 7/1990 | Mallory et al. | |
| 4,959,064 A | 9/1990 | Engelhardt | |
| 5,019,079 A | 5/1991 | Ross | |

(Continued)

FOREIGN PATENT DOCUMENTS

| | | |
|---|---|---|
| EP | 1302170 | 4/2003 |
| EP | 1927322 | 6/2008 |
| WO | 2010067363 | 6/2010 |

*Primary Examiner* — Christian Sevilla
*Assistant Examiner* — Eric S Gibson
(74) *Attorney, Agent, or Firm* — Jacox, Meckstroth & Jenkins

(57) ABSTRACT

A surgical implant comprising a screw element having a screw head, a first thread having a first thread pitch, a second thread having a second thread pitch and an intermediate portion coupling the first and second thread pitches with the first and second thread pitches being different. The implant has a buttressing head associated with the first thread, and it is dimensioned to be larger than a diameter of the first threads to provide external buttressing as the first and second threads compress a first bone and a second bone together.

21 Claims, 3 Drawing Sheets

(56) References Cited

U.S. PATENT DOCUMENTS

| | | |
|---|---|---|
| 5,047,030 A | 9/1991 | Draenert |
| 5,116,337 A | 5/1992 | Johnson |
| 5,120,171 A | 6/1992 | Lasner |
| 5,180,382 A | 1/1993 | Frigg et al. |
| 5,226,766 A | 7/1993 | Lasner |
| 5,259,398 A | 11/1993 | Vrespa |
| 5,334,204 A | 8/1994 | Clewett et al. |
| 5,375,956 A * | 12/1994 | Pennig .................. 411/389 |
| 5,403,136 A | 4/1995 | Mathys |
| 5,417,533 A | 5/1995 | Lasner |
| 5,470,334 A | 11/1995 | Ross et al. |
| 5,492,442 A | 2/1996 | Lasner |
| 5,505,736 A | 4/1996 | Reimels et al. |
| 5,536,127 A * | 7/1996 | Pennig .................. 411/413 |
| 5,562,672 A | 10/1996 | Huebner et al. |
| 5,593,410 A | 1/1997 | Vrespa |
| 5,964,768 A | 10/1999 | Huebner |
| 6,030,162 A * | 2/2000 | Huebner .................. 411/413 |
| 6,053,916 A | 4/2000 | Moore |
| 6,129,730 A | 10/2000 | Bono et al. |
| 6,306,140 B1 | 10/2001 | Siddiqui |
| 6,485,518 B1 | 11/2002 | Cornwall et al. |
| 6,503,252 B2 | 1/2003 | Hansson |
| 6,540,747 B1 | 4/2003 | Marino |
| 6,551,323 B2 | 4/2003 | Doubler et al. |
| 6,648,893 B2 | 11/2003 | Dudasik |
| 6,979,163 B2 | 12/2005 | Brletich et al. |
| 7,223,269 B2 | 5/2007 | Chappuis |
| 7,452,369 B2 | 11/2008 | Barry |
| 7,563,275 B2 | 7/2009 | Falahee et al. |
| 7,608,094 B2 | 10/2009 | Falahee |
| 7,699,878 B2 | 4/2010 | Pavlov et al. |
| 7,708,761 B2 | 5/2010 | Petersen |
| 7,744,630 B2 | 6/2010 | Lancial |
| 7,749,251 B2 | 7/2010 | Obenchain et al. |
| 7,837,713 B2 | 11/2010 | Petersen |
| 7,892,267 B2 | 2/2011 | Lancial et al. |
| 7,901,439 B2 | 3/2011 | Horton |
| 7,993,373 B2 | 8/2011 | Hoy et al. |
| 8,002,812 B2 | 8/2011 | Falahee et al. |
| 8,021,392 B2 | 9/2011 | Petersen |
| 8,043,334 B2 | 10/2011 | Fisher et al. |
| 8,574,273 B2 * | 11/2013 | Russell et al. ............. 606/304 |
| 2002/0169453 A1 | 11/2002 | Berger |
| 2003/0208202 A1 | 11/2003 | Falahee |
| 2004/0087948 A1 | 5/2004 | Suddaby |
| 2004/0097941 A1 * | 5/2004 | Weiner et al. .................. 606/72 |
| 2004/0254575 A1 | 12/2004 | Obenchain et al. |
| 2005/0124993 A1 | 6/2005 | Chappuis |
| 2005/0149030 A1 | 7/2005 | Serhan et al. |
| 2005/0152770 A1 | 7/2005 | Tschakaloff et al. |
| 2005/0267480 A1 | 12/2005 | Suddaby |
| 2006/0025773 A1 * | 2/2006 | Yevmenenko et al. ......... 606/73 |
| 2006/0111779 A1 | 5/2006 | Petersen |
| 2006/0111780 A1 | 5/2006 | Petersen |
| 2006/0200149 A1 | 9/2006 | Hoy et al. |
| 2006/0212034 A1 | 9/2006 | Triplett et al. |
| 2006/0264953 A1 | 11/2006 | Falahee |
| 2007/0112428 A1 | 5/2007 | Lancial |
| 2007/0233092 A1 | 10/2007 | Falahee |
| 2007/0233093 A1 | 10/2007 | Falahee |
| 2007/0233123 A1 * | 10/2007 | Ahmad et al. .................. 606/73 |
| 2007/0233125 A1 | 10/2007 | Wahl et al. |
| 2008/0234758 A1 * | 9/2008 | Fisher et al. .................. 606/309 |
| 2008/0255618 A1 | 10/2008 | Fisher et al. |
| 2008/0255619 A1 | 10/2008 | Schneiderman et al. |
| 2008/0255622 A1 | 10/2008 | Mickiewicz et al. |
| 2008/0255666 A1 | 10/2008 | Fisher et al. |
| 2008/0255667 A1 | 10/2008 | Horton |
| 2008/0262555 A1 | 10/2008 | Assell et al. |
| 2008/0275454 A1 | 11/2008 | Geibel |
| 2009/0036926 A1 | 2/2009 | Hestad |
| 2009/0036927 A1 | 2/2009 | Vestgaarden |
| 2009/0036986 A1 * | 2/2009 | Lancial et al. ............. 623/17.11 |
| 2009/0048675 A1 | 2/2009 | Bhatnagar et al. |
| 2009/0054903 A1 | 2/2009 | Falahee et al. |
| 2009/0076551 A1 | 3/2009 | Petersen |
| 2009/0093851 A1 | 4/2009 | Osman |
| 2009/0099602 A1 | 4/2009 | Aflatoon |
| 2009/0105819 A1 | 4/2009 | Barry |
| 2009/0112264 A1 | 4/2009 | Lins |
| 2009/0125066 A1 | 5/2009 | Kraus et al. |
| 2009/0131986 A1 | 5/2009 | Lee et al. |
| 2009/0163920 A1 | 6/2009 | Hochschuler et al. |
| 2009/0177205 A1 | 7/2009 | McCormack et al. |
| 2009/0187219 A1 | 7/2009 | Pachtman et al. |
| 2009/0192551 A1 | 7/2009 | Cianfrani et al. |
| 2009/0216273 A1 | 8/2009 | Cox |
| 2009/0234394 A1 | 9/2009 | Crook |
| 2009/0234397 A1 | 9/2009 | Petersen |
| 2009/0248082 A1 | 10/2009 | Crook et al. |
| 2009/0248089 A1 | 10/2009 | Jacofsky et al. |
| 2009/0264928 A1 | 10/2009 | Blain |
| 2009/0270929 A1 | 10/2009 | Suddaby |
| 2009/0275954 A1 | 11/2009 | Phan et al. |
| 2009/0275992 A1 | 11/2009 | Phan et al. |
| 2009/0275993 A1 | 11/2009 | Phan et al. |
| 2009/0275994 A1 | 11/2009 | Phan et al. |
| 2009/0299412 A1 | 12/2009 | Marino |
| 2009/0306671 A1 | 12/2009 | McCormack et al. |
| 2009/0312763 A1 | 12/2009 | McCormack et al. |
| 2009/0312798 A1 | 12/2009 | Varela |
| 2009/0312800 A1 | 12/2009 | Chin et al. |
| 2009/0318980 A1 | 12/2009 | Falahee |
| 2010/0068003 A1 * | 3/2010 | Wagner .................. 411/386 |
| 2010/0076490 A1 | 3/2010 | Greenwald et al. |
| 2010/0082065 A1 | 4/2010 | Butler et al. |
| 2010/0087859 A1 | 4/2010 | Jackson, Jr. |
| 2010/0094356 A1 | 4/2010 | Varela et al. |
| 2010/0100135 A1 | 4/2010 | Phan |
| 2010/0114175 A1 | 5/2010 | McKay |
| 2011/0112436 A1 | 5/2011 | Jones et al. |
| 2012/0010659 A1 | 1/2012 | Angert et al. |
| 2012/0010662 A1 | 1/2012 | O'Neil et al. |
| 2012/0010669 A1 | 1/2012 | O'Neil et al. |
| 2012/0022603 A1 | 1/2012 | Kirschman |
| 2012/0197311 A1 | 8/2012 | Kirschman |

* cited by examiner

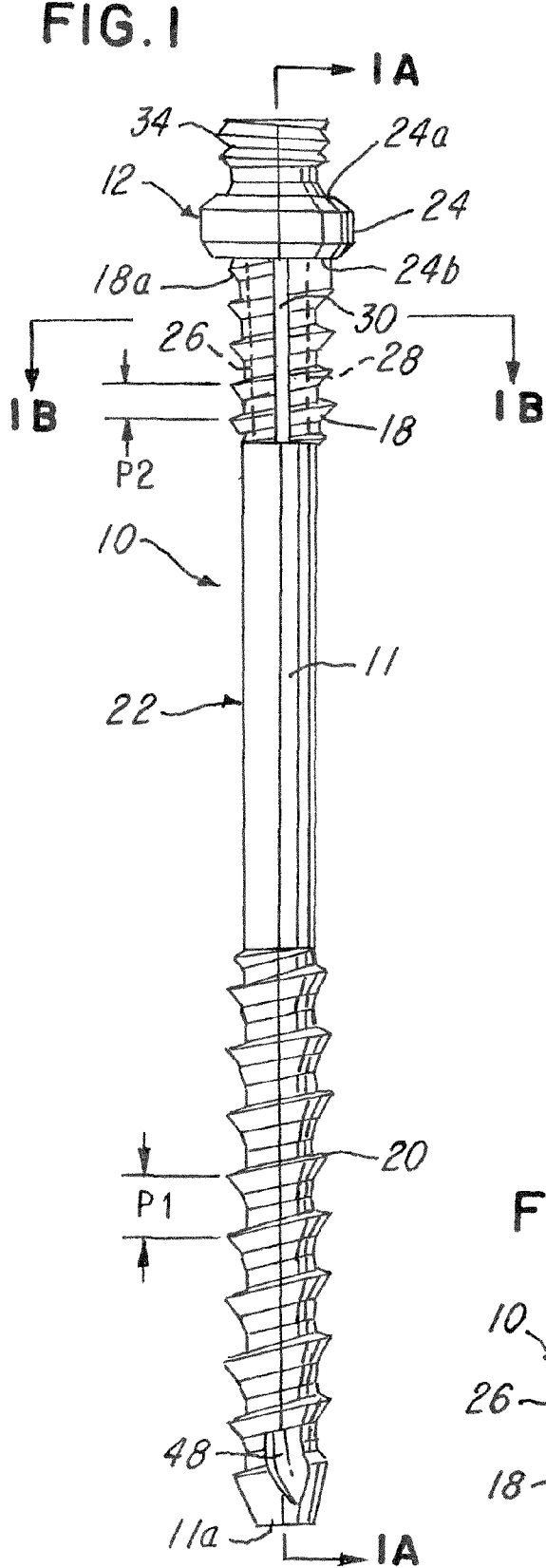
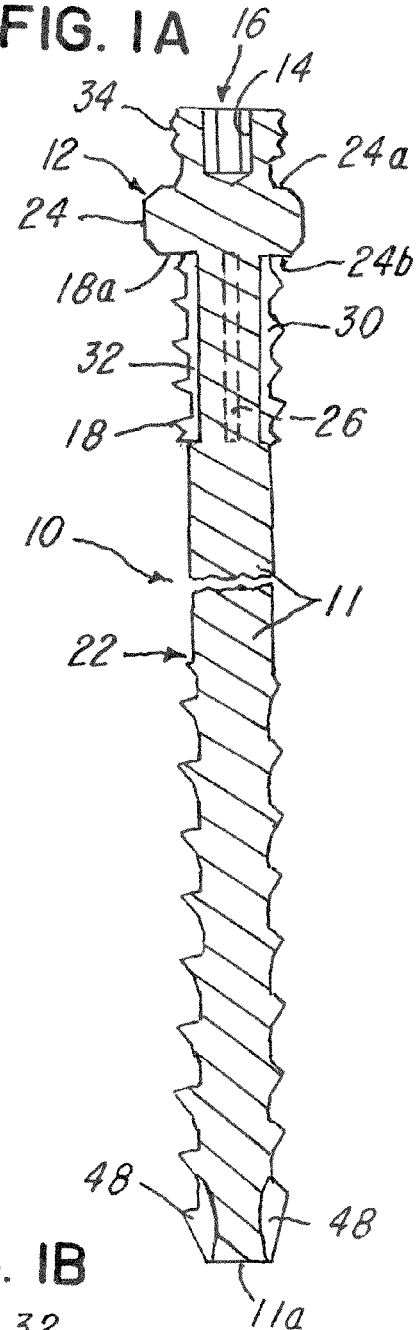
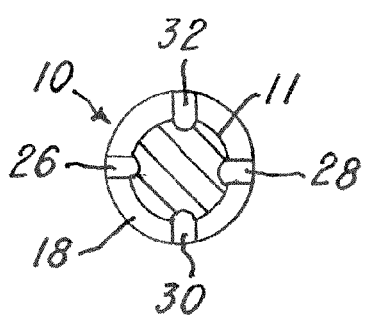
FIG. 1
FIG. 1A
FIG. 1B

SPINAL FACET COMPRESSION SCREW WITH VARIABLE PITCH THREAD ZONES AND BUTTRESS HEAD

CROSS-REFERENCE TO RELATED APPLICATION

The present application claims priority to provisional U.S. Application Ser. No. 61/365,906 filed Jul. 20, 2010, to which Applicant claims the benefit of the earlier filing date. This provisional application is incorporated herein by reference and made a part hereof.

BACKGROUND OF THE INVENTION

1. Field of the Invention

This invention relates to implants, and more particularly, to a spinal facet compression screw comprising a plurality of variable pitch thread zones and a buttress head.

2. Description of the Related Art

The field of spinal implantation burgeons with devices and methods for the achievement of fixation between adjacent vertebrae. The most common devices currently used for the fixation are pedicle screw systems. In a typical pedicle screw system, screws are placed in to the pedicles of adjacent vertebrae and are stabilized together using various separate rod or plate means. An emerging means for achieving fixation of adjacent vertebra is the use of trans-facet fixation. Several devices listed below achieve fixation by placement of a screw or other means though the facet joint. This procedure has the advantage of being significantly less invasive than pedicle screw procedures, since it does not require a separate rod or plate means and only requires two bilateral screws to achieve fixation per level, rather than four in a pedicle screw system. For these reasons, trans-facet fixation has been growing in popularity.

A key goal of trans-facet fixation is the achievement of firm and direct contact of the opposing facet joint surfaces. Such contact is required for the desired bony fusion to take place. The current state of the art relies on the simple tightening of a lag screw to achieve external compression of the facet. This has limited effectiveness due to the limited ability of the relatively fragile facet joint to withstand external screw-tightening forces.

Variable pitch screws have been used in orthopedic surgery, particularly trauma repair, in the past. This is exemplified by the Herbert screw, invented in 1976. These screws, however, rely only on internal compression, and do not benefit from the external screw head buttressing as described in the current invention.

Some of the systems for bone fixation relating to facet fusion are shown or known from U.S. Patent Publications 20030208202 to Falahee; 20040087948 to Suddaby; 20040254575 to Obenchain et al.; 20050124993 to Chappuis; 20050149030 to Serhan; 20050267480 to Suddaby; 20060111779 to Petersen; 20060111780 to Petersen; 20060200149 to Hoy et al.; 20060212034 to Triplett et al.; 20060264953 to Falahee; 20070112428 to Lancial; 20070233092 to Falahee; 20070233093 to Falahee; 20080234758 to Fisher et al.; 20080255618 to Fisher et al.; 20080255619 to Schneiderman et al.; 20080255622 to Mickiewicz et al.; 20080255666 to Fisher et al.; 20080255667 to Horton; 20080262555 to Assell et al.; 20080275454 to Geibel; 20090036926 to Hestad; 20090036927 to Vestgaarden; 20090036986 to Lancial et al.; 20090054903 to Falahee et al.; 20090076551 to Petersen; 20090093851 to Osman; 20090099602 to Aflatoon; 20090105819 to Barry; 20090112264 to Lins; 20090125066 to Kraus et al.; 20090131986 to Lee et al.; 20090163920 to Hochschuler et al.; 20090177205 to McCormack; 20090187219 to Pachtman et al.; 20090192551 to Cianfrani et al.; 20090216273 to Cox; 20090234394 to Crook; 20090234397 to Petersen; 20090248082 to Crook et al.; 20090248089 to Jacofsky et al.; 20090264928 to Blain; 20090270929 to Suddaby; 20090275954 to Phan et al.; 20090275992 to Phan et al.; 20090275993 to Phan et al.; 20090275994 to Phan et al.; 20090299412 to Marino; 20090306671 to McCormack et al.; 20090312763 to McCormack et al.; 20090312798 to Varela; 20090312800 to Chin et al.; 20090318980 to Falahee; 20100076490 to Greenwald et al.; 20100082065 to Butler et al.; 20100087859 to Jackson; 20100094356 to Varela et al.; 20100100135 to Phan; 20100114175 to McKay;

Other systems are shown in U.S. Pat. No. 7,708,761 issued to Petersen; U.S. Pat. No. 7,699,878 issued to Pavlov et al; U.S. Pat. No. 7,608,094 issued to Falahee; U.S. Pat. No. 7,563,275 issued to Falahee et al.; U.S. Pat. No. 7,452,369 issued to Barry; U.S. Pat. No. 7,223,269 issued to Chappuis; U.S. Pat. No. 6,648,893 issued to Dudasik; U.S. Pat. No. 6,540,747 issued to Marino and U.S. Pat. No. 6,485,518 issued to Cornwall et al.

Therefore, what is needed is a new device which draws together the opposing facet joint surfaces via internal compression in addition to external compression.

SUMMARY OF THE INVENTION

In one embodiment of the present invention, internal compression is achieved through the use of two thread zones of differing pitch. Upon placement of this screw, proximal threads are located in the upper facet half and distal threads are located in the lower facet half. Between these threads is a non-threaded screw shaft. By rotating the screw clockwise, rotation of the threads of differing pitches results in a relative movement of the lower facet half towards the upper facet half.

This results in the desired compression. Additionally, a screw head, located above the proximal threads serves to provide additional external buttressing to augment the internal compression.

A surgical implant used, in its preferred embodiment, for the support of spinal vertebrae. The implant comprises a screw element, which is placed through the facet joint of adjacent vertebra. The implant comprises a screw driver attachment zone, a non-threaded buttressing head with a wider diameter than the screw shaft, a proximal narrow-pitch thread, a non-threaded screw shaft, and a distal wide-pitch thread.

In an alternate embodiment, the proximal threads contain a bone-locking feature comprising linear slots in the thread, allowing for bone growth into the thread and helping to prevent the screw from loosening.

In another embodiment, the screw driver attachment zone has an additional set of threads to allow for the engagement of a screw driver locking sleeve. These threads have a handedness opposite of the proximal and distal threads to prevent disengagement of the screw driver locking sleeve.

One object of one embodiment is to provide an improved screw implant that utilizes internal and external compression.

Another object of another embodiment is to provide an improved implant for coupling and/or fusing facet bones of a facet joint.

Still another object of another embodiment is to provide an implant having a plurality of threads with differing thread pitches.

Yet another object of an embodiment is to provide a screw implant having a buttressing head against which a bone may be driven.

Yet another object of an embodiment is to provide a screw implant capable of driving a plurality of bones at different rates.

Another object of an embodiment is to provide a screw implant having locking features, such as a locking slot or aperture, for facilitating ingrowths of bone into the implant.

Another object of an embodiment is to provide an implant having threads associated with the screw head wherein the threads have a thread handedness that is opposite the thread handedness of the threads that engage bone.

In one aspect, one embodiment comprises a surgical implant comprising a screw element having a screw head, a first thread having a first thread pitch, a second thread having a second thread pitch and an intermediate portion coupling the first and second thread pitches, the first and second thread pitches being different and the screw head defining a tool attachment zone, a buttressing head associated with the first thread and being dimensioned to be larger than a diameter of the first threads to provide external buttressing as the first and second threads compress a first bone and a second bone together.

In another aspect, another embodiment comprises a surgical implant comprising an elongated body having a first end and a second end, a screw head associated with the first end, a first thread having a first thread pitch associated with the first end, a second thread having a second thread pitch and an intermediate portion coupling the first and second thread pitches, the first and second thread pitches being different and the screw head defining a tool attachment zone, a buttressing head situated between the first thread and the screw head, the buttressing head being dimensioned to be larger than a diameter of the first threads to provide external buttressing to a first bone as the first and second threads compress a second bone against the first bone.

These and other objects and advantages will be apparent from the following description, the accompanying drawings and the appended claims.

BRIEF DESCRIPTION OF THE DRAWINGS

FIG. 1 is a view of an implant in accordance with one embodiment of the invention;

FIG. 1A is a sectional view taken along the line 1A-1A in FIG. 1;

FIG. 1B is a sectional view taken along the line 1B-1B in FIG. 1;

DETAILED DESCRIPTION OF PREFERRED EMBODIMENTS

Figure 2:
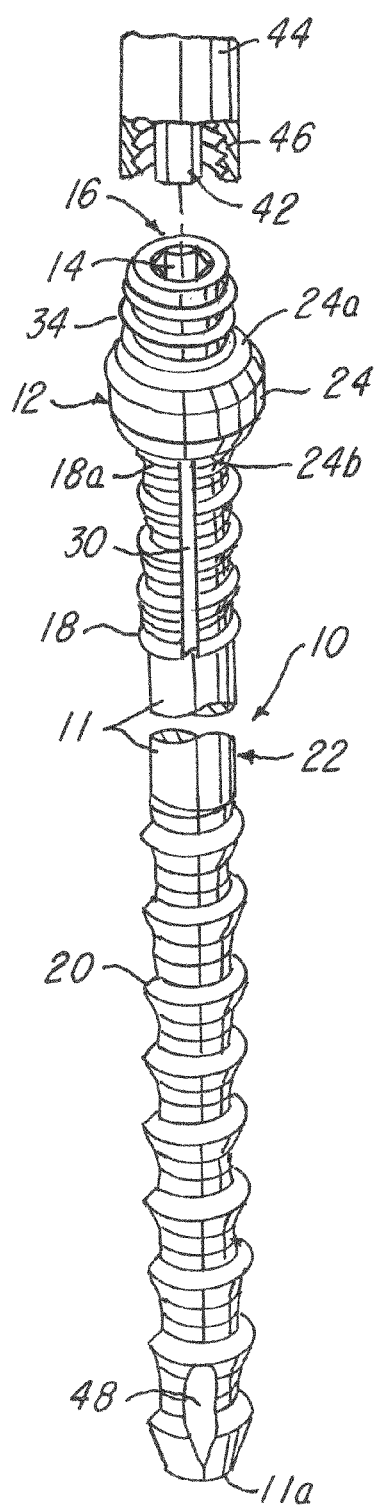
FIG. 2 is perspective view of the implant shown in FIG. 1.
Figure 3:
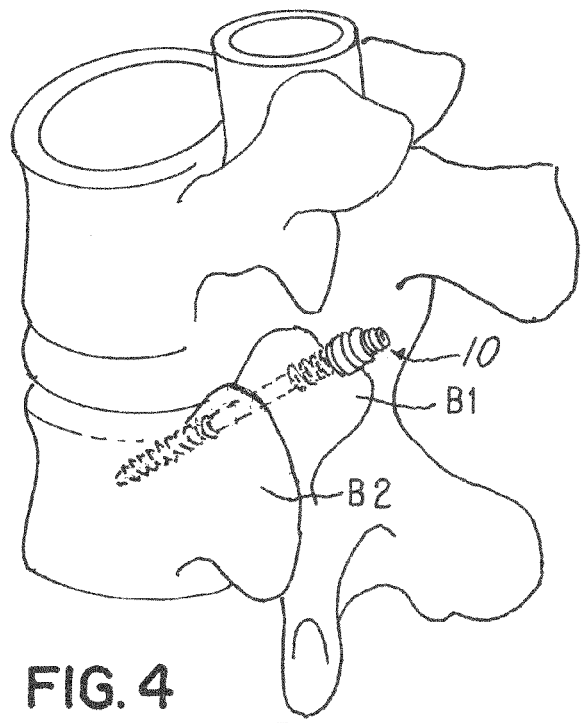
FIG. 3 is a view showing the implant screwed into a facet joint having a first or upper facet bone and a second or lower facet bone of a spinal column.
Figure 4:
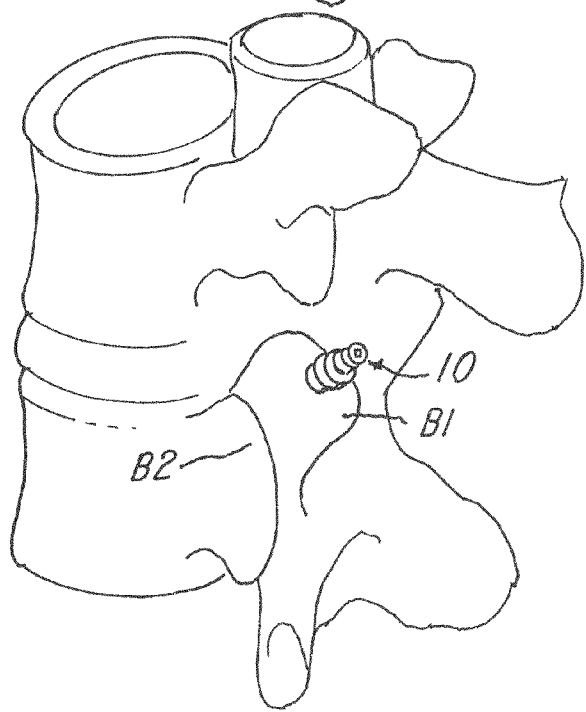
FIG. 4 is another view of the implant after it is screwed into the facet bones to lock the facet bones together.

Referring now to FIGS. 1-5D, a surgical implant 10 is shown. In the embodiment being described, the surgical implant 10 comprises a body 11. The body 11 comprises a screw head 12 having an aperture or tool attachment zone 16. In the illustration, the tool attachment zone 16 comprises an internal wall 14 that defines the aperture or tool attachment zone 16 (FIG. 1A) in the form of a tool receiving aperture for receiving a screw driver 40 (FIG. 2).

The surgical implant 10 further comprises a proximal or first thread 18, a distal or second thread 20 and an intermediate portion 22 that is not threaded and that is integral or monolithically formed with the first thread 18 and second thread 20 as shown. In the illustration being described, it should be understood that pitch distances of each of the first threads 18 and second threads 20 are different. Thus, note in FIG. 1 that a pitch distance P1 for the distal or second threads 20 is larger than a pitch distance P2 of the proximal or first thread 18. Advantageously, the rotation of the first and second threads 18 and 20 results in a relative movement of a first bone B1, such as a lower facet bone (FIGS. 5A-5D), relative to a second bone B2, such as an upper facet bone. This results in a desired compression of the first bone B1 against the second bone B2 as described later herein relative to FIGS. 5A-5D.

As further illustrated in FIGS. 1, 1A and 2, the body 11 of surgical implant 10 further comprises a buttressing head 24. In the illustration being described, the buttressing head 24 is integrally or monolithically formed in the screw body 11 as shown. Note that the buttressing head 24 is generally cylindrical and has a first surface or side 24a and a second surface or side 24b that are generally planar. In the illustration being described, the second surface or side 24b is adjacent to an end 18a of the first or proximal thread 18 and is associated therewith. The buttressing head 24 is larger in diameter than both the first and second threads 18 and 20, and provides a buttress or stop that facilitates providing external buttressing as the first and second threads 18 and 20 compress the first bone B1 and the second bone B2 together. In other words, as the first thread 18 drives the second bone B2 leftward (as viewed in FIGS. 5A-5D) upon rotation of the body 11, the second bone B2 ultimately engages the second side 24b and the first bone B1 is driven by the second or distal thread 20 toward the second bone B2 until they engage and are in compression. Thus, the first and second threads 18 and 20 provide an internal compression of the first and second bones B1 and B2, and the surface 24b of buttressing head 24 provides a surface 24b against which the first bone B1 can drive and compress the second bone B2, thereby providing an external compression.

As mentioned earlier, the pitch distance P1 (FIGS. 1 and 1A) of the second or distal threads 20 is larger than the pitch distance P2 of the first or proximal thread 18 which means that the first and second threads 18 and 20 drive their respective bones B2 and B1 (as viewed in FIG. 5A-5D) at different leads or rates. In this regard, the rate of driven movement of the first bone B1 is greater than the rate of the driven movement of the second bone B2, as illustrated in FIGS. 5A-5D.

Note that the intermediate portion 22 of the body 11 is not threaded and has a diameter smaller than the diameter of the first and second threads 18 and 20 and the buttressing head 24. This further facilitates driving the first and second bones B1 and B2 together.

In the illustration being described, the surgical implant 10 further comprises a plurality of locking slots or apertures 26, 28, 30 and 32 (FIG. 1B) that are generally elongated slots or apertures located in the first threads 18. Although not shown, the second threads 20 could also comprise one or more locking slots or apertures. In the illustration being described, the locking slots or apertures 26-32 are elongated and generally parallel to an axis of the body 11, as best illustrated in FIG. 1A. In the embodiment being described, the body 11 comprises locking slots or apertures 26, 28, 30 and 32, that are radially spaced about an axis A (FIG. 1A) of the body 11, as best illustrated in FIG. 1B. In the illustration being described, the locking slots or apertures 26-32 are generally elongated and linear, but it should be understood that they could comprise another configuration, such as a spiral or helical configuration or shape.

In the illustration being described, the locking slots or apertures 26-32 facilitate allowing for bone growth over and/or into the body 11 of the surgical implant 10 after the surgical implant 10 is screwed into a patient. The locking slots or apertures 26-32 facilitate preventing the surgical implant 10 from loosening after the surgical implant 10 is screwed into the patient by providing areas for such bone growth. In the illustration being described, the embodiment is shown as having four locking slots or apertures 26-32, but it should be appreciated that more or fewer locking slots or apertures 26-32 could be provided in at least one of both a plurality of the first threads 18, the second threads 20 and/or in the intermediate portion 22. In the illustration being described, the locking slots or apertures 26-32 are located in the first thread 18.

As is conventionally known, the second threads 20 may have a plurality of notched out areas 48 (FIGS. 1-1A) to facilitate the start of the surgical implant 10 into the first and second bones B1 and B2.

In another embodiment, the screw head 12 comprises a third thread 34 (FIGS. 1, 1A and 2) at the tool attachment zone 16 to allow for engagement of and connection to a surrounding or tool locking sleeve 44 (FIG. 2). In the illustration being described, the handedness of the third thread 34 is opposite the handedness of each of the first and second threads 18 and 20. For example, if the first and second threads 18 and 20 are right-handed threads, then the third thread 34 is left-handed, and vice versa, if the first and second threads 18 and 20 are left-handed, then the third thread 34 are right-handed. The opposite handedness facilitates preventing disengagement of the surgical implant 10 from the screw driver 40. Note in FIG. 2 that the screw driver 40 comprises a male screw driver tool 42 that is received in the mating female opening in the tool attachment zone 16 and a surrounding sleeve 44 having threads 46 that mate with the third thread 34. In the illustration being described, the opposite handedness of the first and second threads 18 and 20 from that of the third threads 34 facilitates preventing disengagement of the screw driver 40 from the male screw driver tool 42. It should be understood that the sleeve 44 remains stationary during rotation of the screw driver tool 42.

Note that the first or proximal threads 18 have pitch distance P2 that is less than pitch distance P1 than the second or distal threads 20. This feature causes the bone B1 that receives the second or distal thread 20, such as a facet joint surface, to move at a rate R1 toward the buttressing head 24. The opposing bone surface B1*a* (FIGS. 5A and 5D) that receives the first or proximal thread 18 moves at a rate R2 that is slower than the rate R1. Stated another way, the second or distal thread 20 and the first or proximal thread 18 move opposing bone surfaces B1*a* and B2*b*, respectively, toward the buttressing head 24 at the first and second rates R1 and R2 until the second bone surface B2*a*, such as an opposing facet joint surface, comes into contact with the surface 24*b* of the buttressing head 24. As mentioned earlier, by rotating the screw clockwise in the example, rotation of the first and second threads 18 and 20 of the differing pitches results in a relative movement of the lower bone, such as a lower facet half toward an upper bone, such as the upper facet half, until the upper facet half is situated and compressed between the buttressing head 24 and the lower facet half thereby resulting in a desired compression. Again, note that the external buttressing head 24 buttresses the compression.

Figure 5A:
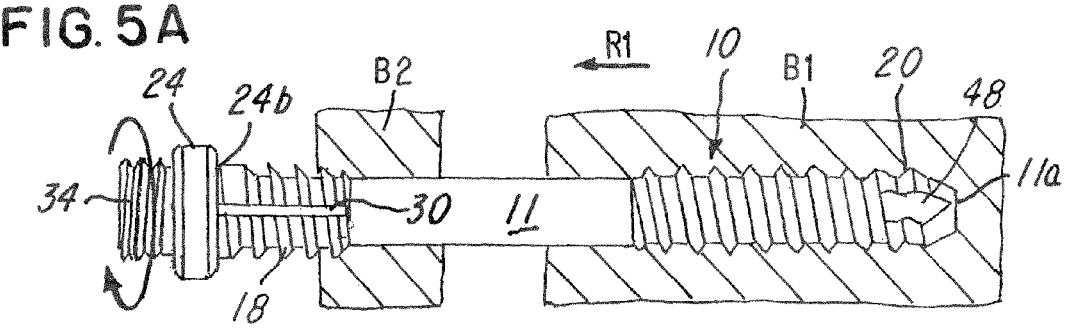
FIGS. 5A-5D illustrate the relative movement of the first bone relative to a second bone during rotation of the implant.
Figure 5B:
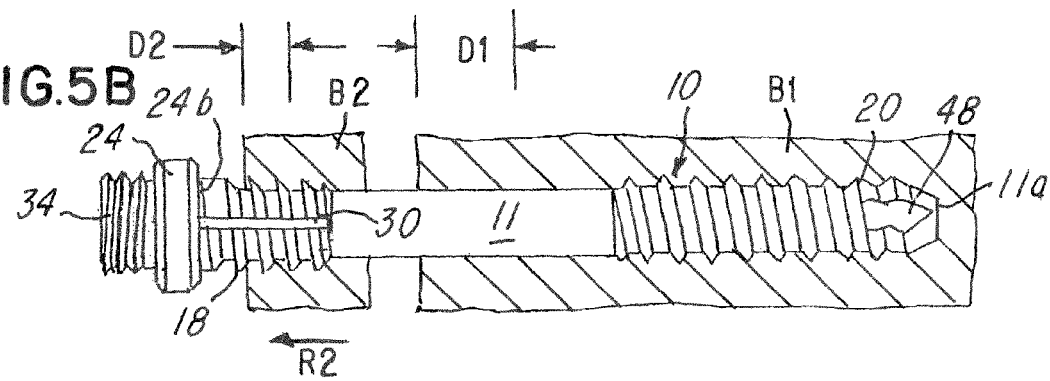
Figure 5C:
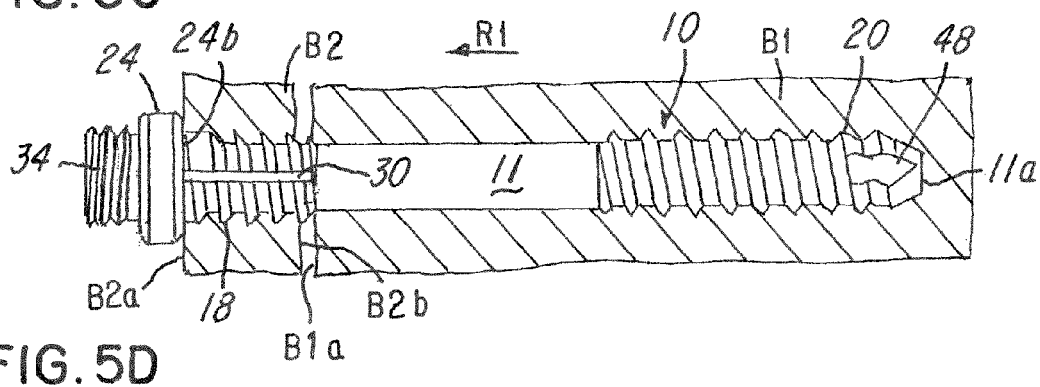
Figure 5D:
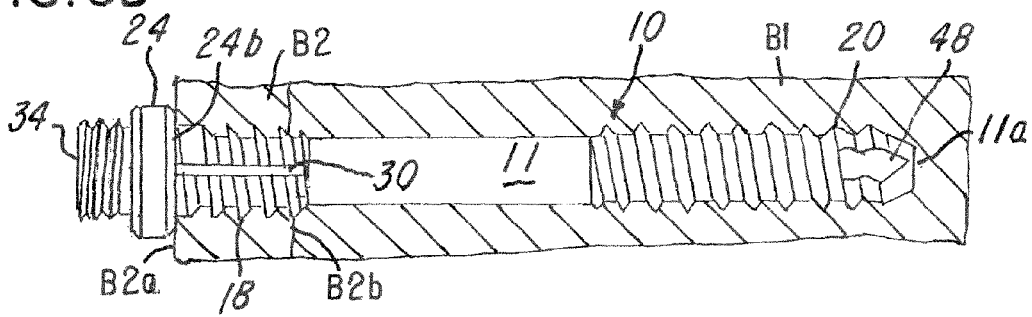

As shown in FIGS. 5A-5D, the distal end 11*a* (FIG. 1) of surgical implant 10 is screwed into the first bone B1 and the proximal thread is screwed into the second bone B2. When the surgical implant 10 is rotated clockwise, the distal thread 20 is screwed into the bone B1 and drives it leftward (as viewed in FIGS. 5A-5C) a distance D1 as shown in FIGS. 5A and 5B. Substantially simultaneously, the first or proximal threads 18 are screwed into the bone B2 and drive it relative to the buttressing head 24 leftward (as viewed in FIGS. 5A-5C) a distance D2 as shown in the comparison of FIGS. 5A, 5B and 5C. This relative movement of the bones B1 and B2 continues as illustrated in FIGS. 5C and 5D during rotation of the body 11 of surgical implant 10 until a surface B2*a* of the bone B2 engages the buttressing head 24 and the surface B1*a* of bone B1 engages the generally opposing surface B2*b* as illustrated in FIGS. 5C and 5D. In this regard, notice that the bone surface B1*a* engages the bone surface B2*b* and drives it toward the buttressing head 24, thereby compressing the bones B1 and B2 together and compressing the bone B2 against the buttressing head 24. The external compression and internal compression facilitate securing the bones B1 and B2 together.

Advantageously, the system, method and implant described herein provide a means for fusing bones, especially the facet bones of a facet joint. The surgical implant 10 provides additional buttressing and compression of at least one or both of the bones that are fused or secured together.

While the system, apparatus and method herein described constitute preferred embodiments of this invention, it is to be understood that the invention is not limited to this precise system, apparatus and method, and that changes may be made therein without departing from the scope of the invention which is defined in the appended claims.

What is claimed is:

1. A surgical implant comprising:
   a screw element defining a bone screw for compressing a first bone and a second bone together, said screw element having a screw head, a first thread having a first thread pitch, a second thread having a second thread pitch and an intermediate portion coupling said first and second threads, said second thread pitch being greater than said first thread pitch and said second thread being longer and having a longer lead than said first thread;
   said screw head defining a tool attachment zone adjacent a buttressing head, said tool attachment zone being threaded; and
   said buttressing head between said tool attachment zone and said first thread and being dimensioned to be larger than a diameter of said first thread to provide external buttressing as said first thread and said second thread drive and compress said first bone and said second bone, respectively, together;
   wherein said buttressing head is not threaded and said first thread drives said first bone at a rate that is smaller than a rate at which said second thread drives said second bone;
   wherein said first thread is proximally located adjacent said buttressing head and said second thread is distal and spaced from said first thread;
   wherein said screw element comprises a plurality of locking slots to facilitate allowing for bone growth over said screw element and helping to prevent said screw element from loosening;
   wherein said first thread being a proximal thread and having a first set of locking slots and said second thread being a distal thread and having a second set of locking slots.

2. The surgical implant as recited in claim 1 wherein both said intermediate portion and said buttressing head are not threaded.

3. The surgical implant as recited in claim 1 wherein said plurality of locking slots are linear.

4. The surgical implant as recited in claim 1 wherein said plurality of locking slots are located in said first thread.

5. The surgical implant as recited in claim 1 wherein said screw head comprises third threads at said tool attachment zone to allow for engagement of a tool locking sleeve.

6. The surgical implant as recited in claim 5 wherein said third threads have a handedness that is opposite the handedness of each of the first and second threads.

7. The surgical implant as recited in claim 1 wherein said first thread pitch and said second thread pitch are different so that when said first thread threadably engages and drives said first bone to be fused at a first rate and said second thread threadably engages and drives said second bone to be fused toward said first bone at a second rate, wherein said second rate is greater than said first rate.

8. The surgical implant as recited in claim 1 wherein said buttressing head has a generally planar bone-engaging surface at an end of said first threads.

9. The surgical implant as recited in claim 1 wherein said first threads are proximal threads and said second threads are distal threads, said first and second threads driving said first bone and second bone, respectively, towards said buttressing head at different rates.

10. The surgical implant as recited in claim 9 wherein said buttressing head has a generally planar surface for engaging bone.

11. A surgical implant defining a bone screw for compressing a first bone and a second bone together comprising:
an elongated body having a first end and a second end;
a screw head associated with said first end;
a first thread having a first thread pitch associated with said first end, a second thread having a second thread pitch and an intermediate portion coupling said first and second threads, said second thread pitch being greater than said first thread pitch and said second thread being longer than said first thread;
said screw head defining a tool attachment zone adjacent a buttressing head, said tool attachment zone being threaded; and
said buttressing head situated between said first thread and said screw head;
said buttressing head being dimensioned to be larger than a diameter of said first thread to provide external buttressing to said first bone as said first thread and said second thread drive and compress said second bone against said first bone, respectively;
wherein said buttressing head is not threaded and said first thread drives said first bone at a rate that is smaller than a rate at which said second thread drives said second bone;
wherein said first thread is proximally located adjacent said buttressing head and said second thread is distal and spaced from said first thread;
wherein said elongated body comprises a plurality of locking slots;
wherein said first thread being a proximal thread and having a first set of locking slots and said second thread being a distal thread and having a second set of locking slots.

12. The surgical implant as recited in claim 11 wherein said intermediate portion and said buttressing head are not threaded.

13. The surgical implant as recited in claim 11 wherein said plurality of locking slots are linear.

14. The surgical implant as recited in claim 11 wherein said plurality of locking slots are located in said first thread.

15. The surgical implant as recited in claim 11 wherein said screw head comprises third threads to allow for engagement of a tool locking sleeve.

16. The surgical implant as recited in claim 15 wherein said third threads have a handedness that is opposite the handedness of each of the first and second threads.

17. The surgical implant as recited in claim 16 wherein said surgical implant is provided with a screw driver having a screw driver locking sleeve having threads that mate with the third threads and that has an internal screw driver for rotatably driving said surgical implant.

18. The surgical implant as recited in claim 11 wherein said first thread pitch and said second thread pitch are different so that when said first thread threadably engages and drives said first bone to be fused at a first rate and said second thread threadably engages and drives said second bone to be fused toward said first bone at a second rate, wherein said second rate is greater than said first rate.

19. The surgical implant as recited in claim 11 wherein said buttressing head has a generally planar bone-engaging surface at an end of said first threads.

20. The surgical implant as recited in claim 11 wherein said first threads are proximal threads and said second threads are distal threads, said first and second threads driving said first bone and second bone, respectively, towards said buttressing head at different rates.

21. The surgical implant as recited in claim 20 wherein said buttressing head has a generally planar surface for engaging bone.

* * * * *